United States Patent [19]

Sitek

[11] 4,060,717
[45] Nov. 29, 1977

[54] ACID TESTER

[75] Inventor: George J. Sitek, Stevensville, Mich.

[73] Assignee: Leco Corporation, St. Joseph, Mich.

[21] Appl. No.: 627,194

[22] Filed: Oct. 30, 1975

[51] Int. Cl.$^2$ .................. G06F 15/20; G01N 27/26
[52] U.S. Cl. ................................. 364/497; 204/1 T;
204/195 R; 204/195 M; 324/71 R; 364/900
[58] Field of Search ............... 235/151.35, 151.3;
340/172.5; 204/193, 194, 195 R, 195 M, 195 G,
1 T, 1 H, 1 B; 137/87, 88, 93; 324/30 R, 33, 71
R; 23/252 R

[56] References Cited

U.S. PATENT DOCUMENTS

| Re. 24,222 | 9/1956 | Patnode et al. | 204/195 M |
|---|---|---|---|
| 2,672,441 | 3/1954 | White | 204/195M |
| 3,431,182 | 3/1969 | Frant | 204/1 B |
| 3,497,449 | 2/1970 | Urban | 235/151.35 |
| 3,528,778 | 9/1970 | McKaveney et al. | 204/195 M |
| 3,672,962 | 6/1972 | Frant et al. | 204/195 M |
| 3,768,499 | 10/1973 | Dziomba et al. | 137/93 |
| 3,889,255 | 6/1975 | Pettersen | 324/30 R |
| 3,920,969 | 11/1975 | Berglas | 235/151.3 |

OTHER PUBLICATIONS

Manahan, S., Fluoride Electrode as a Reference in the Determination of Nitrate Ion; Analytical Chemistry, vol. 42, no. 1, Jan. 1970, pp. 128–129.

Rechnitz, G., Ion Selective Electrodes; C & EN; June 12, 1967, pp. 146–158.

Primary Examiner—Malcolm A. Morrison
Assistant Examiner—Errol A. Krass
Attorney, Agent, or Firm—Price, Heneveld, Huizenga & Cooper

[57] ABSTRACT

An instrument that determines the HF and the HNO$_3$ concentration or other mixed acids or single acid of an acid bath measures the potential difference between a fluoride ion selective electrode and a reference electrode and the potential difference between a hydrogen ion selective electrode and the reference electrode. The electrode voltages are applied to a control circuit including a microprocessing unit for calculating and displaying the acid concentrations of the bath and for compensating for the nonlinearity of the measured voltages as well as the interdependence of the two voltages. Also, means are provided for calculating and displaying percent metal concentrations.

21 Claims, 3 Drawing Figures

ACID TESTER

BACKGROUND OF THE INVENTION

The present invention relates to acid testers and more particularly to a system for measuring the concentration of hydrofluoric and nitric acid in solution with each other.

Pickling baths such as used in the manufacture of stainless steel include in many instances the combination of hydrofluoric acid with nitric or other strong acids having free hydrogen ions. Inasmuch as both acids include free hydrogen ions, it has in the past been difficult, if not impossible, to measure the concentration of the constituent acids of the bath by conventional means. This is true even though acid testing meters utilizing electrodes have been commercially available and can be used to measure either hydrofluoric or nitric acid concentrations when only one of the acids is present in solution.

Efforts have been made to develop a titration process for the measurement of hydrofluoric and nitric acid concentrations in stainless steel pickling baths but the resultant process is very cumbersome and has not been commercially practical or successful.

More recently, a hydrogen ion selective membrane electrode of the general type disclosed in U.S. Reissue Pat. No. 24,222 has been utilized in combination with a fluoride electrode and a reference electrode common to both electrodes to provide voltages representative of the hydrogen and fluoride ion concentration in a pickling bath including both hydrofluoric and nitric acids. By utilizing a plurality of solutions of known concentrations of hydrofluoric and nitric acids and plotting a graph of the known concentrations versus the voltage measured by the hydrogen selective electrode and the fluoride ion selective electrode, curves are plotted which correspond to the respective concentrations of hydrofluoric and nitric acids for the measured electrode voltages.

An instrument has been developed incorporating such electrodes and graphical representations utilizing antilog amplifiers and suitable numerical control circuits for subtraction, multiplication and addition for processing the measured electrode voltages and providing a digital display of the acid concentration for pickling baths employing both hydrofluoric and nitric acids. Although such a system represents a significant improvement over the cumbersome titration process and permits the direct readout of acid concentrations utilizing a three electrode system, the instrument developed lacks the flexibility desired for expanding the system to other acid combinations and represents electrically an elementary approach to the solution of the problem.

As a result of the state of the art at this time, most users of mixed acid baths have not attempted to continuously monitor hydrofluoric and nitric acid concentrations but merely replace the acid bath or refresh the bath periodically or do so when an inspection of the resultant product indicates the pickling bath needs changing.

SUMMARY OF THE INVENTION

The system of the present invention eliminates the difficulties of the prior art and greatly improves upon the electrical circuitry employed in the prior art to provide an improved system of greater reliability and speed of operation with virtually unlimited flexibility in measuring acid concentrations wherein hydrofluoric acid is combined with other hydrogen ion acids such as nitric, hydrochloric, sulfuric acids, or any other acid.

Acid testers embodying the present invention employ in combination with a fluoride and hydrogen ion selective electrode operating with a reference electrode, a microprocessing unit coupled to the electrodes for correlating the signal representative of the electrode voltages according to a predetermined relationship and correcting for nonlinearities in the voltages measured to provide output signals representative of the concentration of each of the acids in the bath.

By utilizing a microprocessing unit, the system's flexibility is greatly increased inasmuch as the correlation and linearity correction information can be provided in storage means such as programmable read-only memories and easily changed for use of the instrument for different acid combinations. Also, by use of a microprocessing unit, the control of the instrument through the various sequences of operation required when handling several different acids and the calibration of the instrument is facilitated.

These and other advantages and objects of the present invention will become readily apparent upon reading the following description thereof together with reference to the accompanying drawings in which:

DETAILED DESCRIPTION OF THE PREFERRED EMBODIMENT

Figure 1:
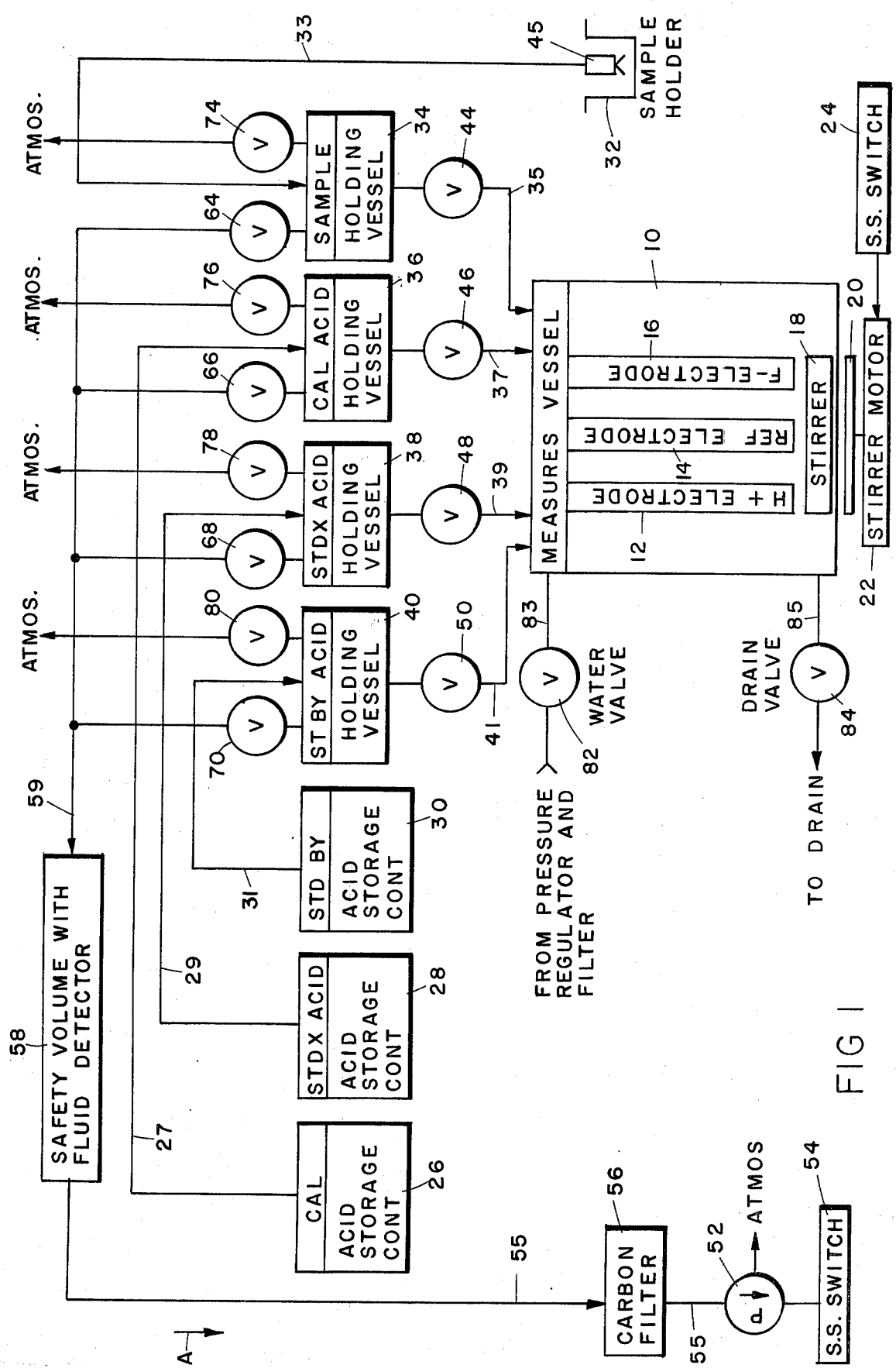
FIG. 1 is a block diagram of the acid handling structure of the instrument embodying the present invention.

Referring initially to FIG. 1, the acid tester includes a measurement vessel 10 which receives the various acid solutions and into which there is positioned a hydrogen ion selective membrane electrode 12, a reference electrode 14 and a fluoride ion selective electrode 16. Continuous stirring of the fluid in the measurement vessel 10 is accomplished by means of a magnetic stirrer rod 18 rotated by a rotatable magnet 20 positioned on the outside of the vessel below the stirring rod 18 and driven by motor 22, in turn coupled to a power supply and actuated by means of a solid state switch 24. Vessel 10 and the remaining acid storage and holding vessels and the various conduits intercoupling the vessels are made of an acid impervious material such as polyvinyl chloride (PVC). The reference electrode 14 is commercially available from Orion Research, Inc., Model No. 90-04, as is the fluoride (F−) electrode 16, Model No. 94-09A.

The H+ electrode 12 is a membrane electrode suitable for the determination of acidity in strongly acidic and corrosive solutions. This electrode employs a heterogeneous membrane including a polystyrene base and a cationic exchanging functional group specifically sulfonic acid or carboxyl groups and an internal solution of one molar nitric acid and 0.1 molar hydrochloric acid. The electrode can be constructed according to the teachings of U.S. Reissue Pat. No. 24,222 issued on Sept. 18, 1956 to H. W. Patnode et al. the disclosure of which is incorporated herein by reference.

The instrument includes storage containers 26, 28 and 30 for storing, respectively, an acid calibration solution, an acid standardizing solution and an acid standby solution. The calibration acid solution consists of a one molar nitric and a one molar hydrofluoric acid solution. The standardizing acid solution consists of a solution of three molar nitric and 0.5 molar hydrofluoric acid while the standby acid solution consists of a weak acid such as one molar nitric acid. The purposes of these various acid solutions are described in detail below.

The calibration storage container 26 is coupled to the calibration acid holding vessel 36 by means of a conduit 27. The standardization acid storage container 28 is coupled to the holding vessel 38 by means of a conduit 29. The standby acid storage container 30 is coupled to the holding vessel 40 by means of conduit 31 and the sample holder 32 is coupled to the holding vessel 34 by means of a conduit 33. Conduit 33 includes in the preferred embodiment an elevatable and lowerable nozzle element 45 permitting the sample holder to be positioned on a supporting platform on the instrument and the nozzle then lowered in position within the sample holding vessel. In order to transport acids from the storage containers and from the sample holding vessel 32 into which the acid specimen is placed, into the measurement vessel 10, a plurality of holding vessels are employed including a sample acid vessel 34, a calibration acid vessel 36, a standardizing acid vessel 38 and finally, a standby acid vessel 40. Each of these vessels is positioned physically above the measurement vessel permitting transportation of acid within the holding vessels into the measurement vessel by gravity through associated empty valves 44, 46, 48 and 50, respectively, and interconnecting conduits 35, 37, 39 and 41 as shown in FIG. 1.

In order to draw acid from the storage vessels or the sample holding vessel into the holding vessels, an evacuation pump 52 is provided and actuated by a solid state switch 54 and power supply (not shown) to withdraw air in a direction indicated by arrow A in FIG. 1 from the various holding vessels. The air evacuation path includes conduit 55, a carbon filter 56 positioned upstream the vacuum pump 52, as is a safety volume 58 constituting an enclosed vessel having a pair of platinum contacts positioned at the bottom thereof for detecting the existence of any fluid which may be inadvertently drawn into the safety volume during the evacuation of the holding vessels. The intake of the safety volume is coupled to each of the holding vessels through a conduit 59 and a plurality of fill valves 64, 66, 68 and 70 associated with vessels 34, 36, 38 and 40, respectively, as shown in FIG. 1. Also coupled to each of the holding vessels is an atmospheric bleeder valve 74, 76, 78 and 80 coupled to vessels 34, 36, 38 and 40, respectively, as shown in FIG. 1. A pressurized source of water is selectively supplied to the measurement vessel 10 through a water valve 82 and conduit 83 for flushing the vessel as required. Vessel 10 is emptied into a suitable drain with a dead volume by means of a drain valve 84 coupled to the bottom of the vessel by a conduit 85.

Normally, when the instrument is not in use, vessel 10 will be filled with the standby solution to protect the electrodes. This is achieved by actuating valve 70 associated with the standby acid holding vessel 40 with valves 50 and 80 closed. Pump 52 is then actuated to draw a vacuum on the standby acid holding vessel which in turn draws acid from its associated storage container 30 for a predetermined (i.e., operator selected) period of time calculated to at least partially fill the holding vessel. Typically, 100 cc is used.

Once the holding vessel 40 is at least partially filled with the standby acid from container 30, valve 70 is turned off by the control including circuit 214 (FIG. 2) and valves 50 and 80 opened permitting the standby acid to spill into the measuring vessel 10 for providing protection to the electrodes within the measurement vessel. Before the measuring vessel is used for an analysis, the clean cycle is run. This cycle empties the vessel by opening chain valve 84, flushing the vessel with water by actuation of valve 82 while agitating the flushing water with stirrer 18.

The calibrate acid solution from container 26 is then supplied to the measurement vessel 10 in the same manner as discussed above with respect to the standby acid, only by selectively actuating valves 66, then 46 and 76. Once the electrode voltage is read and the calibration measurement completed, the calibration acid is then drained, followed by another clean cycle. Next, the measurement vessel is filled with the standardization solution through the opening of valve 68 first and then valves 48 and 78. The standardization and calibration fluids are used to establish, respectively, the scale factor for the instrument as well as the Y intercept points as discussed below and do so by means of the control circuits shown in FIG. 2. After measurement of the standardization acid has taken place, the standardization solution is drained from the measurement vessel and another clean cycle run.

About 250 cc of specimen solution is placed in container 32. The unknown acid forming the specimen to be analyzed is then introduced into the measurement vessel by the actuation of valves 64 and 44 and 74 with the sample holder 32 placed within the instrument and nozzle 45 lowered therein such that the specimen solution can be drawn into the holding vessel 34. In order to assure accurate results, the measurement vessel is purged using about half of the specimen which is then drained. Next, the remaining portion of the specimen solution is introduced into vessel 10 through holding vessel 34. Once the measurement is complete to provide an analysis of the specimen solution, the measurement vessel is then cleaned by another clean cycle.

It is seen, therefore, that the fluid flow system shown in FIG. 1 provides the plumbing necessary for safely transporting acids within the system without the necessity of the operator being needlessly exposed to the acid which is highly corrosive and somewhat dangerous while also providing a system for cleaning contaminants from the measurement vessel so that an accurate analysis can be run on the specimen solution. This technique for handling acids is known except that a standardization solution for determining the scaling factor and thus its associated structure has not been used. Having described the fluid container and transportation system for the acid tester of the preferred embodiment of the invention, a description of the electrical control circuit for actuating the various valves shown in FIG. 1 as well as receiving voltages from the electrodes and processing the signals therefrom to provide a display of the acid concentration is presented with respect to FIGS. 2 and 3 now discussed.

Figure 2:
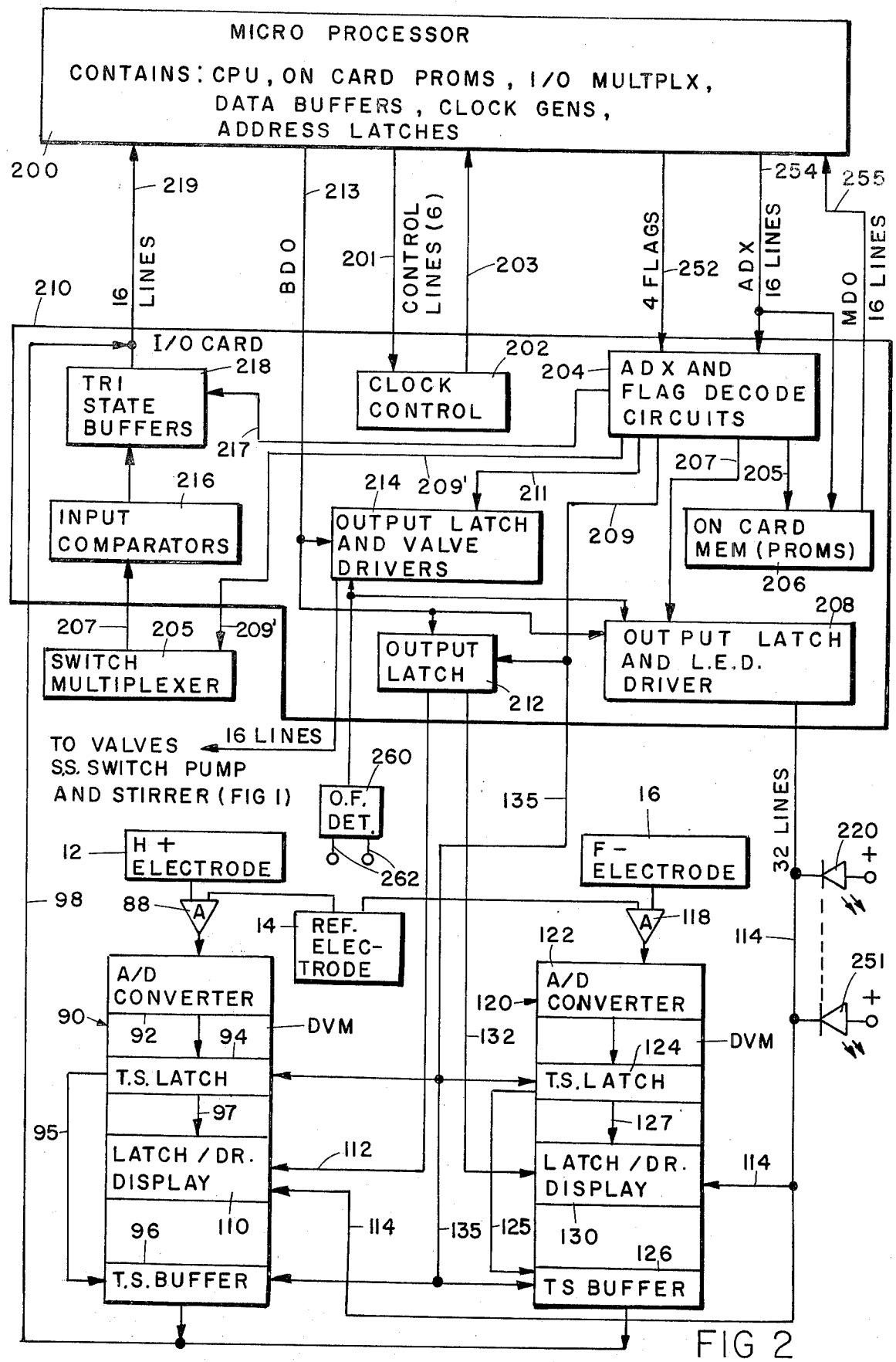
FIG. 2 is an electrical circuit diagram in block form of the electrical system of the acid tester of the present invention.

In the electrical control circuit shown in FIG. 2, the H+ electrode 12 and the F− electrode 16 are electrically coupled to amplifiers 88 and 118, respectively, as is reference electrode 14. Each of the electrodes 12 and 16 generates an analog voltage in the order of a few millivolts representative of the detected hydrogen and fluoride ion concentration respectively. These output voltages are then converted into digital output signals for subsequent processing by the data processing means 200 including a central processing unit. The output voltage from electrode 12 is applied to a DVM module 90 by means of differential amplifier 88. Module 90 includes an A/D converter for converting the analog input voltage into 16-bit binary coded decimal format and the output of the converter is coupled to a tristate latch circuit 94. Latch 94 includes a sixteen line output 95 coupled to a tristate buffer circuit 96 which applies the digital output signal information representative of the ion concentration detected by electrode 12 to the microprocessor 200 by means of a sixteen line conductor 98 and via the input/output module 210 as seen in FIG. 2. The tristate latch 94 also includes a sixteen line output 97 for applying the digital output signals directly to a latch driver and display circuit 110 which is actuatable to display the measured voltage from electrode 12 or a variety of other digital information including the nitric acid concentration which is applied to latch 110 via sixteen line input conductor 112 and controlled by the CPU by lines 135 as described below.

Similarly, the fluoride electrode 16 is coupled to a second DVM module 120 by means of an amplifier 118. Module 120 also includes an A/D converter 122 having its output coupled to a tristate latch 124, in turn having a sixteen line output 125 coupled to a tristate buffer 126. An additional sixteen line output 127 of tristate latch 124 is coupled to a latch driver and display circuit 130 also receiving input information from the input/output card 210 via sixteen input lines 132 and controlled by the CPU by lines 135. Control lines 135 consist of four lines, one of which is used for controlling the operation of the latches 94 and 124 simultaneously, two of which are coupled to buffers 96 and 126 for alternately controlling the flow of data therefrom, and the final line used for clamping the DVMs. The output of buffer 126 is also coupled to the microprocessor 200 via sixteen lines 98 which include 16 conductors used for four digit binary coded decimal data representative of the measured electrode voltage.

The microprocessor 200 together with the interface circuits of the input/output module 210 control the operation of the instrument according to operator input commands from a switch multiplexer circuit 205 which includes a plurality of operator accessible switches. In the preferred embodiment, multiplexer 205 includes one hundred and four switches utilized to provide output command signals on eight output lines 207 coupled to the input/output module 210. The digital switches of the multiplexer are interrogated by the microprocessor for reading preprogrammed switch codes included in the switches by a sixteen line input 209. The switch multiplexer includes a power on-off switch, analyze, calibrate, standardize, standby, stop and percent/molar switches, percent metal switch, as well as digital thumb wheel switches serving as storage means for setting the time duration for operation of, for example, the vacuum pump 52 and the various alarm limits for the system. Additionally, included in the switch multiplexer 205 are digital switches for entering the weight of the specimen such that the instrument can be utilized as described below for providing an indication of the metal ion content of the specimens in addition to the hydrofluoric and nitric acid concentration in percent by weight. The switches included in circuit 205 are physically mounted on a front panel control for the instrument with the primary control switches being readily accessible and the programming digital thumb wheel type switches are mounted behind a door inasmuch as they are only periodically employed.

In addition to the control inputs from the switch multiplexer 205, the microprocessor and its associated input/output module 210 provide 32 lines of output via lines 114 in FIG. 2, which lines are employed for controlling the decimal point for the DVM modules 90 and 120, as well as for actuating a plurality of light emitting diodes indicating to the operator the status of the instrument in addition to the digital readout provided. There are 31 light emitting diodes identified in FIG. 2 as 220 to 251. These diodes are coupled to the thirty-one output lines 114 to provide to the operator, for example, an out of range or warning condition so that corrective action can be taken. By programming of eighteen addresses in digital switches included within the switch multiplexer 205 and actuating an associated ad-call switch, the operator can select several stored parameters from memory for display by units 110 and 130. In addition, the light emitting diodes will indicate the particular mode of operation of the instrument as well as other status information to notify the operator of an operational condition of the system requiring action.

The microprocessor 200 is a commercially available National Semiconductor Model No. IMP-16C and integrally includes a central processing unit, a plurality of programmable read-only memories for receiving program instructions controlling the operation of the various arithmetic units included within the CPU, an input-/output multiplexer for controlling the flow of data between the microprocessor 200 and the input/output module 210, data buffers for the temporary storage of data as well as clock generators and address latches for the control of data flow within the microprocessor. The input/output module 210 includes a clock control circuit 202 receiving clock pulses from the microprocessor via lines 201 and applying synchronized output clock pulses to the microprocessor via output conductors 203. The purpose of the clock control 202 is to synchronize the programmable read-only memories within the microprocessor with the external supplementary PROMs included within the input/output module in block 206. The control of the flow of data between the microprocessor and the output peripherals is maintained by the address and flag decode circuit 204 of the input/output card which includes four address lines 205 coupled to the PROM unit 206, eight control lines 207 coupled to the output latch and LED drive circuit 208, five lines of output control signals 209, four of which are applied to the DVM modules via four conductors 135 and one line of which is applied to an output latch circuit 212 for strobing data inputted to the latch into the displays 110 and 130. Circuit 204 also is coupled to an output latch and valve driver circuit 214 by means of conductor 211 for strobing output signals stored in the latch circuit 214 to the various valves and solid state switches shown in FIG. 1. Circuit 204 also includes a 16 line output 209' which, as discussed above, is coupled to the switch multiplexer 205 for reading switch codes contained therein and outputting the information to input comparators 216. Comparators 216 read the input data and apply it to the tristate buffers 218. Circuit 204 actuates the tristate buffer circuit 218 via line 217 to read input data into the CPU within the microprocessor 200 by means of the sixteen lines 219 of input data coupling the tristate buffer 218 to the microprocessor 200.

The binary data output from the microprocessor is applied to the three output latch circuits 208, 212 and 214 by means of 16 data lines 213 as shown in FIG. 2. The address and flag decoding circuit receives flags from the microprocessor via flag lines 252 and addresses by sixteen data lines 254 for receiving address data also applied to the memory circuit 206. Circuit 206 in turn provides memory data output via 16 data lines 255 to the microprocessor 200. The overflow detector circuit 260 has a pair of input terminals 262 which are coupled to the platinum probes within the safety volume 58 (FIG. 1) and provide an output signal to circuits 214 and 208 for actuating circuit 208 to light an LED display indicating an overflow condition exists and at the same time, actuating solid state switch 54 through latch circuit 214 (FIG. 1) to deactuate pump 52.

The internal operation of the microprocessor and its supplemental memory 206 with circuit 204 for handling input and output data is easily understood by those skilled in the art. The programming of the PROMs used in the preferred embodiment to provide the control functions and more specifically, to correlate the measured voltages from electrodes 12 and 16, as well as for correction of the nonlinearity in the voltages as well as the interdependence of the measured voltages and the overall function of control circuit of FIG. 2 is unique and best understood by reference to the flow diagram shown in FIG. 3 and the following description.

Figure 3:
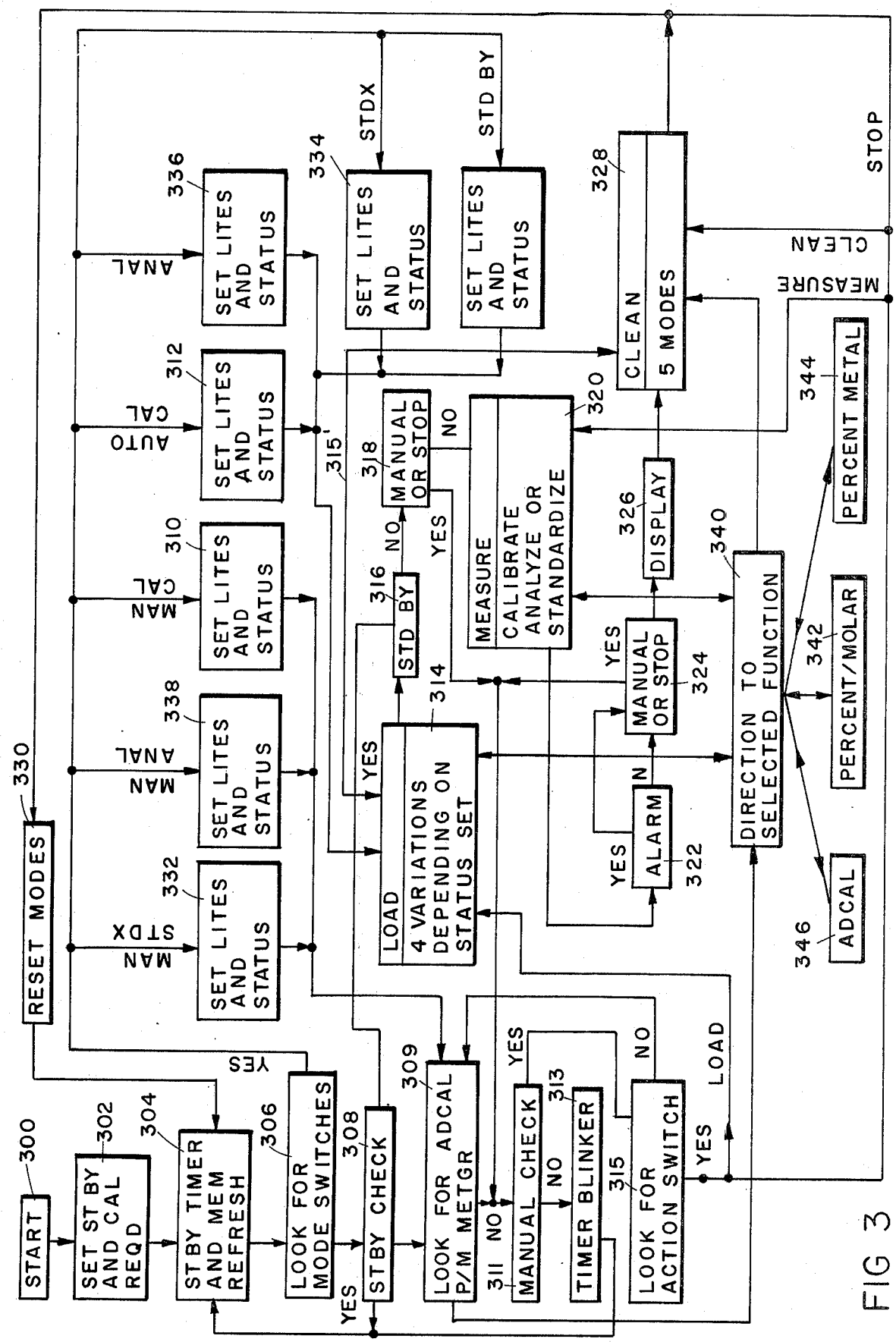
FIG. 3 is a flow diagram of the operation of the microprocessing unit shown in FIG. 2 for controlling the operation of the instrument embodying the present invention.

FIG. 3 indicates the program functions for the electrical control circuit of FIG. 2 and the resultant instrument operation. The sequence of operation is initiated, as indicated by the start block 300 in the upper left-hand corner of the FIG. 3 diagram, by the operator actuating the power on switch in circuit 205 in response to which the stored program sets the instrument in the standby mode of operation by setting the read-only memory of the microprocessor with a standby status word indicating the system is in standby. Also, a LED indicating to the operator that calibration is required is actuated via circuits 204 and 208. These functions are represented by block 302 in FIG. 3. In standby, the read/write memories of microprocessor 200 are refreshed with the addresses of the various subroutines employed, as indicated by block 304, and the control switches of circuit 205 are scanned to see if a mode switch, either automatic or manual, has been actuated by the operator (block 306). The standby status word is then read to see if the system is in standby and the microprocessor cycles through functional blocks 304, 306 and 308, repeatedly checking for the actuation of a mode switch by the operator. Normally, when the instrument is not in use, it will be placed in the standby mode of operation. The modes available in manual are calibrate, standardize or analyze while the automatic mode switches are calibrate, standardize, analyze or standby. If no mode switch has been actuated by the operator, the system remains in the standby loop with the standby acid in the measurement vessel until a mode switch is actuated.

The normal sequence of automatic operation would be for the operator to first actuate the auto-calibrate switch included in switch multiplexer 205 (FIG. 2). Inasmuch as the calibrate required status light is actuated, only automatic or manual calibrate switch actuation is detected by the control circuit. Actuation of either automatic or manual calibrate sets the indicator lights and status by transferring from the PROM memory the valve actuation information and the various constants such as time of actuation of the valves, range limits and the like and transfers this data into RAM memory for use by the CPU. This function is indicated by the manual calibrate step 310 and the automatic calibrate step 312. When automatic calibrate has been actuated, the control sequence proceeds to the loading sequence 314 whereupon the standby status word is read and if in standby, valve 84 is opened for a time sufficient to empty the standardization solution from the measurement vessel followed by a clean cycle of operation (functional block 328). After cleaning, the standby status word is reset to indicate the system is no longer in standby and the sequence returns to the load sequence 314. Calibration acid solution is then introduced, as noted earlier, by the actuation of the pump 52 (FIG. 1) for a predetermined time followed by actuation of the fill and bleed valves 46 and 76. During each of the action modes (i.e., load, measure and clean), the stop switch is continuously monitored and if actuated by the operator, the action status words are reset and the action mode is terminated. The system then checks to see if the load program was a standby program as indicated by block 316. If it was, the processor returns to the standby loop and checks for the operation of mode switches as discussed above. If not, as is the case, the system checks to see if a stop switch in circuit 205 has been actuated as indicated by block 318. If the stop switch has been actuated by the operator, the sequence proceeds to the system monitor loop including 311, 313, 315, 304, 306, 308 and 309 indicated by a timer blinker comprising flashing front panel LED (block 313) to indicate to the operator the instrument is in the system monitor mode and a mode switch must again be actuated to proceed with an analysis. Typically, the stop switch would not be actuated unless an abnormality in acid handling occured. Thus, typically, once the loading step has been completed by the timing out of the predetermined filling time for the calibration acid in the measurement vessel, the control system proceeds to the measurement process for the selected calibrate routine as indicated by block 320.

If the manual calibrate switch has been actuated, upon termination of the load sequence the system check at block 318 indicates manual operation and the sequence 311, 315 and 309 (i.e., manual loop) is run in which an action mode switch actuation is looked for. If the stop switch was actuated, the system is reset through functional block 330 and cycles through the system monitor loop identified above.

For the calibrate measure routine, the stirrer 18 is continuously agitating the solution and voltage between the reference electrode 14 and the F— electrode 16 is measured at a first time $t_1$ and a subsequent time $t_2$ (for example, 15 seconds after $t_1$) providing two voltage measurements $EFt_1$ and $EFt_2$. Next, the absolute value of the difference of these voltages is compared with a predetermined drift value stored in memory to ascertain whether or not the voltages are maintained within a preset drift limit, which limit is programmed into the instrument by means of a thumb wheel digital switch included in the switch multiplexer 205. If within the preset tolerance, the voltages between electrode 12 and the reference electrode 14 are measured at times $t_1$ and $t_2$, which voltages are referred to hereinafter as $EHt_1$ and $EHt_2$ and compares the absolute value of the differences of these voltages to a similarly preprogrammed drift value. If either of the electrode voltages differences are greater than the stored drift values, an alarm in the form of a light emitting diode actuated by a signal from output line 114 of circuit 208 in FIG. 2 is actuated (block 322).

If within tolerance, the calibration proceeds by subtracting from the measured voltage $EFt_2$ the value predicted for the known calibration solution and comparing the absolute value of the difference of these two voltages with a predetermined range value to ascertain that the measured voltage for the calibration solution is within range. This process is repeated for the H+ electrode 12 and if either of the voltages is out of tolerance, an overrange alarm is actuated. If within tolerance, the values $EFt_2$ and $EHt_2$ are stored in RAM memory associated with the microprocessor as $EO_2$ and $EO_1$ respectively. The calibrate required light is then extinguished. Again, the stop switch and the manual status is checked and if either has been detected, the system proceeds as discussed above with reference to block 318.

In the event a drift out of tolerance or overrange condition is detected, the calibration cycle is terminated and the program function goes to the manual check block 311. If the stop switch had been actuated by the operator during the measure mode, the action mode status is reset and the system returns to the system monitor loop as discussed above with reference to the calibration step, only through decisional block 324.

If within the range and tolerance, the digital readout displays 110 and 130 provide a readout of the concentration of the calibration solution either in molar or percentage weight. This is indicated by block 326 in the flow diagram of FIG. 3. The purpose of the calibration mode is to determine and store the electrode voltages at a first known concentration of HF and $HNO_3$. The calibrate concentrations are displayed continuously until the next measurement cycle or when one of the modes indicated by blocks 342, 344 or 346 is called for. The clean mode of operation is automatically initiated as indicated by block 328. The clean mode is run after each measurement during calibrate, standardize and analyze and in addition, if the loading is called for when the standby solution is in the measurement vessel, cleaning is achieved as indicated by the interconnection of blocks 314 and 328 by lines 315. The clean mode has been discussed above with reference to FIG. 1 and it basically involves the flushing of the measurement vessel with water by the actuation of valves 82 and 84 and agitation by the stirrer 18.

After the clean mode, the previously set lights and status information for the selected mode of operation (in this case, auto-calibrate) are reset, as indicated by block 330, and the system cycles in the system monitor mode, again checking for the actuation of a mode switch by the operator as indicated by block 306.

Typically, the manual or automatic standardization switch is then actuated and the light and status data for standardize are transferred from the PROM and the digital switches in the switch multiplexer circuit 205 into the RAM memory of the microprocessor 200, as indicated by blocks 332 or 334 for the manual and automatic modes respectively.

The purpose of the standardize mode is to ascertain the measured values of two constants $K_1$ and $K_2$ which correspond to the slope of the electrode voltage versus acid concentration curves for the acids in the standardization solution which are representative of acid concentrations to be measured. Thus, while the calibration step ascertains the intercept point for the acid concentration at a one molar level, the standardization measurement step determines basically the slope of the correction curve at a point remote from the calibration point to provide accurate compensation for the nonlinearity of the electrode voltage versus concentration curve representative of the response of the detecting electrodes as well as the interdependence of the measured electrode voltages as a function of the hydrofluoric and nitric acid concentrations. If the auto-standardize switch has been actuated, the system proceeds, as discussed above, through the load step 314 to the measurement routine 320 except that the standardize acid solution is loaded into the measurement vessel.

During standardization, first the drift values at $t_1$ and $t_2$ are checked as noted above with reference to the calibration process. Next, the absolute value of the difference between $EFt_2$ (consisting of the F− electrode 16 voltage) and a predicted and preprogrammed value for the standardization solution fluoride ion electrode is compared with a stored range value to ascertain whether or not the actual measured voltage is within a preselected tolerance. Similarly, the difference of the $EHt_2$ voltage (the measured hydrogen ion electrode 12 voltage) and a stored predicted value is compared with a stored range value. In the event that either of these comparisons is out of range, an alarm, as indicated in block 322, is actuated and the instrument returns to manual operation as discussed above. This prevents the automatic dumping of the standardize acid from the measurement vessel and allows the operator to determine the reason for the alarm and to remeasure the acid manually.

If the measured values are within the range, the microprocessor interrogates the predicted values for $K_1$ and $K_2$ entered into constant switches in the switch multiplexer 205 through circuit 204 and sets the $HNO_3$ concentration to 3.00. Next, the following equations 1–7 are solved and the actual value of constant $K_2$ in memory is incremented or decremented until the solution of equation 7 for $HF = 0.5$.

$$HFP = \text{Antilog} \frac{EO_2 - EFt_2}{K_2} \quad 1)$$

$$HNOO = \text{Antilog} \frac{EHt_2 + 3.3 - EO_1}{K_1} \quad 2)$$

$$FAK = 4.339 - (1.769\ HNOO) + (0.5645\ HNOO^2) \\ - (0.1002\ HNOO^3) + (0.008698\ HNOO^4) \\ - (0.0002926\ HNOO^5) \quad 3)$$

$$HX = \frac{\mp 9.976 + \sqrt{99.53 - (19.95\ HNOO)}}{.9547\ HNOO} \quad 4)$$

$$HNO_3 = \text{Antilog}\left[\left(\frac{EHt_2 + 3.3 - EO_1}{K_1}\right) - \left(\frac{HX \cdot FAK \cdot HNOO \cdot HFP}{K_1}\right)\right] \quad 5)$$

Substitute $HNO_3$ for $HNOO$ and solve equation 4) above for $HX^1$ \quad 6)

$HF = HX^1 \cdot HNO_3 \cdot HFP$ \quad 7)

The equations 1–7 are solved by the microprocessor by programming of the PROMs in a conventional manner and which can be accomplished in any number of well-known antilog multiplication, division, summing and subtraction programming.

The actual value of $K_1$ in memory is then incremented or decremented until the value for the $HNO_3$ solution equals 3.00 at which time the concentrations are displayed, as indicated by block 326, and actuates the K update indicator LED. The system then cleans the measurement vessel and resets the lights and status, as indicated by blocks 328 and 330, returning to the system monitor loop 304, 306 and 308 until the operator is ready to analyze the unknown specimen.

Either manual or automatic analyzing switches are actuated by the operator to initiate the analyze phase by setting the lights and status information required for an analyze cycle as indicated by blocks 338 and 336 respectively. At this time, constants $EO_2$ and $EO_1$ have been determined from the calibration step by the use of the known concentration calibration solution as are the constants $K_2$ and $K_1$ from the standardize solution and process. These constants correspond to measured values of voltages which, of course, are subject to some change with external conditions as well as the electrode aging, etc. and, therefore, are updated periodically by the process discussed above. The system is thus, at this point in time of the cycle of operation, ready to analyze the unknown specimen. The weight of 100 cc of specimen is then entered into a digital switch in multiplexer 205 and approximately 250 cc is placed in container 32 and loaded, as indicated by the functional block 314, by controlling the valves and pump, as discussed above, and the instrument proceeds to the measure function indicated by block 320 for analysis passing through checks 316 and 318 as discussed above.

During analysis, the drift of the electrode voltages is again checked as discussed above with reference to the calibrate step. If in range, the voltage of electrode 16 is checked with the stored upper limit for acid concentrations normally incurred as is the voltage of electrode 12 using a separate stored upper limit. If either of the measured voltages are in excess of the upper permissible limits, an out of tolerance alarm is actuated and the analysis is aborted by returning to the manual loop as indicated by block 322. Constants $K_1$ and $K_2$ from the digital switches are inserted if the operator has not run a standardization and thus the constant update light is extinguished. If the operator has updated these constants by running a standardization, the actual $K_1$ and $K_2$ values stored in RAM memory are employed to again solve the equations 1-7 supra using the values of $EHt_2$ and $EFt_2$ measured by the electrodes immersed in the specimen solution. This provides, depending upon the display selected by the operator, either a percent by weight readout of the specimen $HNO_3$ and HF concentrations or a molar concentration. If no alarm or stop signal has occurred, these results are displayed on the digital displays 110 and 130, as indicated by block 326, after which the measurement vessel is cleaned (block 328) and the system reset (block 330). The system then returns to the system monitor loop including blocks 304, 306 and 308. Equations 1-7 supra are valid for acid combinations other than the HF and $HNO_3$ example given.

After the analysis in system monitor loop or between action modes in manual operation, the system will not be in standby and the various operator selected control switches discussed in detail below and including a percent metal switch will be interrogated as indicated by functional block 309. Typically, after determining the acid concentrations, the operator will actuate the percent metal switch to ascertain metal content of the specimen. Actuation of the percent metal switch causes the microprocessor to proceed to the percent metal operational block 344 through the directional function 340. In this mode of operation, utilizing the stored previously ascertained molar content of the specimen and the premeasured weight of 100 cc of the specimen entered into a digital switch by the operator, the following equation is solved by the microprocessor to provide the percent metal ion content of the specimen.

$$\% \text{ Metal} = \frac{\left(\begin{array}{c}\text{gram weight of} \\ \text{100 cc of specimen}\end{array}\right) - \left[\begin{array}{c}3.33 \times HNO_3 \text{ Molar} \\ + .57 \, HF \text{ Molar}\end{array}\right]}{\text{gram weight of 100 cc of specimen}}$$

The constant 3.33 is an acid density constant ($ADK_1$) for $HNO_3$ while the constant 0.57 is an acid density constant ($ADK_2$) for HF. These constants will, of course, be changed for acid baths of different acids than the example given.

The primary difference between manual and automatic modes of operation resides in the loading of the measurement vessel and the subsequent cleaning step which in manual is accomplished by actuating a load switch followed by the actuation of a measure switch to provide the calibrate, standardize or analyze sequence which, when completed, is followed by the actuation of a clean switch for cleaning the measurement vessel. Thus, in the manual mode indicated by functional block 311, the manual sequence proceeds to functional block 315 to look for the actuation of a specific action switch for the above noted sequences of operation.

In order to provide diagnostic information whereupon the operator can utilize the system's pair of digital voltmeters, 18 memory locations are provided in which the operator can display various systems through the ad-call subroutine 346 which is achieved by actuating one of several ad-call switches in multiplexer 205. The ad-call parameters, some of which are stored in memory and include the following possible display information, can be displayed.

1. The electrode voltages directly
2. The voltage of each electrode at time $t_1$ can be recalled from memory
3. The voltage of each electrode at time $t_2$ can be recalled from memory
4. $EO_1$ and $EO_2$ can be recalled from memory
5. Constants $K_1$ and $K_2$ can be recalled from memory
6. The molar concentration for each acid can be recalled from memory and displayed
7. The percent by weight concentration of each acid can be displayed
8. The grams metal concentration can be recalled from memory and displayed
9. The system includes a counter for the number of analyses run between calibrates and this number can be displayed. When this number reaches a predetermined value set by the operator in a digital switch, the calibrate required light is actuated The programming of the PROMs associated with the microprocessor to provide the functions indicated in the flow chart of FIG. 3 is within the skill of one skilled in the art and is accomplished by the utilization of programmable read-only memories included within the microprocessor and in the preferred embodiment, also included in the memory card 206 (FIG. 2). It will become apparent to those skilled in the art that various modifications to the system can be achieved to accommodate for different acids or combinations of acids utilizing the concepts of the present invention and the scope of the present invention is to be ascertained by reference to the accompanying claims.

The embodiments of the invention in which an exclusive property or privilege is claimed are defined as follows.

1. An acid testing instrument for use in combination with electrodes which are fluoride ion and hydrogen ion selective for determining the constituent acid concentrations in a bath including hydrofluoric and another acid having free hydrogen ions comprising:
    circuit means coupled to said electrodes for providing digital output signals representative of the ion concentration detected by said electrodes;
    a microprocessor and interface circuit means coupled to said microprocessor for handling input and output data and control signals to and from said microprocessor, said microprocessor coupled to said circuit means for receiving said digital output signals wherein said microprocessor includes a central processing unit (CPU) and storage means, a read-only memory and a switch multiplexer having operator actuated digital switches therein permitting the operator to select system parameters for controlling said CPU to correlate and process said digital output signals in a predetermined manner to provide display output signals representative of the concentration of acids being tested; and
    display means coupled to said interface circuit means for receiving and displaying said display output signals as acid concentrations.

2. The instrument as defined in claim 1 wherein said circuit means includes an amplifier for each of said electrodes and coupled to said electrodes and an analog-to-digital converter coupled to each amplifier for providing said digital output signals.

3. The system as defined in claim 2 wherein display means comprises digital readout means and said instrument further includes a plurality of indicator lights coupled to said interface circuit means to be selectively actuated thereby for displaying the operational status of said instrument.

4. The instrument as defined in claim 3 wherein said instrument includes a measurement vessel into which said electrodes are positioned, means for supplying acid solutions to said measurement vessel, said supplying means coupled to said interface circuit means for receiving control signals therefrom, said supplying means including an overflow detector coupled to said interface circuit means for deactuating said supplying means is an excessive amount of acid solution is supplied by said supplying means.

5. An acid testing instrument including a measurement vessel for receiving acid solutions and into which there is positioned measurement electrode means, said instrument comprising:
    means for supplying a calibration acid solution to said measurement vessel;
    means for supplying a standardization acid solution of different concentration than said calibration acid solution to said measurement vessel;
    means for supplying a specimen acid solution to said measurement vessel; and
    measurement control means coupled to said electrode means and to each of said supplying means for sequentially actuating said supplying means for filling said measurement vessel with calibration acid, standardization acid and finally, specimen acid and measuring the output from said electrode means for each solution to determine two points on an acid concentration and electrode output correlation curve for the different acid concentrations of the calibration and standardization acid solutions and using this data for providing calibration and standardization data used in the determination of the concentration of the specimen acid solution.

6. The instrument as defined in claim 5 for use in determining the acid concentrations of the specimen solution wherein said instrument includes a first electrode for the measurement of hydrogen ion concentration and a second electrode for the measurement of fluoride ion concentrations and said measurement control means includes computation circuit means for generating electrical signals in the form of:

$$HFP = \text{Antilog} \frac{EO_2 - EFt_2}{K_2} \quad 1)$$

$$HNOO = \text{Antilog} \frac{EHt_2 + 3.3 - EO_1}{K_1} \quad 2)$$

$$FAK = 4.339 - (1.769\ HNOO) + (0.5645\ HNOO^2) \\ - (0.1002\ HNOO^3) + (0.008698\ HNOO^4) \\ - (0.0002926\ HNOO^5) \quad 3)$$

$$HX = \frac{-9.976 + \sqrt{99.53\ [-] \pm (19.95\ HNOO)}}{.9547\ HNOO} \quad 4)$$

$$\text{Acid 1} = \text{Antilog}\left[\left(\frac{EHt_2 + 3.3 - EO_1}{K_1}\right) - \left(\frac{HX \cdot FAK \cdot HNOO \cdot HFP}{K_1}\right)\right] \quad 5)$$

Substitute $[HNO_3]$ Acid 1 for $HNOO$ and solve equation 4) above for $HX^1$ \quad 6)

$$\text{Acid 2} = HX^1 \cdot [HNO_3]\ \text{Acid 1} \cdot HFP \quad 7)$$

where:
    $EO_2$ and $EO_1$ are signals derived from the electrode voltages when in the calibration solution;
    $K_2$ and $K_1$ are signals derived from the electrode voltages when in the standardize solution; and
    $EFt_2$ and $EHt_2$ are signals derived from the electrode voltages when in the specimen solution and where HFP, HNOO, FAK, HX, $HX^1$ are operators in the form of electrical signals derived from said computation circuit means solving the relationships of formulas 1–7, and wherein Acid 1 is an electrical signal representing the concentration of a first acid in the specimen solution and Acid 2 is an electrical signal representing the concentration of a second acid in the specimen solution.

7. The instrument as defined in claim 6 and including display means coupled to said measurement control means and wherein the signals representative of Acid 1 and Acid 2 are displayed as the respective acid concentrations by said display means.

8. The instrument as defined in claim 7 wherein the weight of a known volume of a pickling bath specimen solution including HF and $HNO_3$ acids and metal ions is stored by said measurement control means and wherein said computation circuit means further generates electrical signals in the form of:

$$\%\ \text{Metal} = \frac{\left(\begin{array}{c}\text{gram weight of}\\ 100\ \text{cc of specimen}\end{array}\right) - \left[\begin{array}{c}ADK_1 \times HNO_3\ \text{Molar}\\ +\ ADK_2\ HF\ \text{Molar}\end{array}\right]}{\text{gram weight of 100 cc of specimen}}$$

where $ADK_1 = 3.33$ for $HNO_3$ and $ADK_2 = 0.57$ for HF and said percent metal by weight is displayed by said display means.

9. The instrument as defined in claim 8 wherein said measurement control means includes a microprocessor and an interface circuit coupling said microprocessor to said display means and to said electrodes.

10. An acid testing instrument for use in combination with electrodes which are fluoride ion and hydrogen ion selective for determining the constituent acid concentrations in a bath including hydrofluoric and another acid having free hydrogen ions, said instrument comprising circuit means coupled to said electrodes for measuring the voltage output of said electrodes when said electrodes are immersed successively in a calibration acid solution of a known acid concentration and a standardization acid solution of a known concentration different than the concentration of said calibration acid solution and a specimen acid solution of unknown concentration, said voltage output being representative of acid concentration said instrument including memory means coupled to said circuit means for storing signals from said circuit means representative of the acid concentrations of said calibration and standardization acid solutions, display means coupled to said circuit means, and control means coupled to said circuit means and to said memory means and actuated by an operator to selectively recall from said memory means said signals and applying said signals to said display means for displaying the concentrations of said known acid solutions permitting an operator to determine the accuracy of the display by said instrument of said known acid solution.

11. The instrument as defined in claim 10 wherein said memory means stores signals representative of the acid concentrations of each solution at a first and a second time and said circuit means includes means for comparing the differences in detected concentrations with a predetermined drift limit for providing a drift alarm signal if the predetermined limit is exceeded and wherein said control means further includes operator actuated means for selecting said drift limit.

12. The instrument as defined in claim 10 wherein said circuit means comprises a microprocessor and interface circuit means for coupling said microprocessor to said display means and said control means.

13. The instrument as defined in claim 12 wherein said control means comprises a switch multiplexer including a plurality of operator selectable digital switches for controlling the operation of said microprocessor.

14. An acid testing instrument for use in combination with electrodes which are fluoride ion and hydrogen ion selective for determining the constituent acid concentrations in a bath including hydrofluoric and another acid having free hydrogen ions comprising:
   first circuit means coupled to said electrodes for providing output signals representative of the ion concentration detected by said electrodes;
   second circuit means coupled to said first circuit means for receiving and processing said output signals according to a predetermined interrelationship of constituent acids included in said bath for providing display output signals representative of the concentration of constituent acids of said bath;
   operator programmable means for storing signals representative of a predetermined acid concentration limit for at least one electrode;
   said second circuit means including means for comparing said predetermined limits with the measured acid concentrations and for providing an alarm output signal in the event said limits are exceeded; and
   alarm output means coupled to said comparator means and responsive to said alarm signal to provide an operator alarm.

15. The instrument as defined in claim 14 wherein said first circuit means comprises amplifier means coupled to said electrodes for providing amplified output signals therefrom and analog-to-digital converter means coupled to said amplifier means for providing said output signals in a digital format.

16. The instrument as defined in claim 15 wherein said second circuit means comprises a digital processing circuit including memory means for controlling the processing of said output signals.

17. The instrument as defined in claim 16 wherein said memory means provides signals for controlling said digital processing circuit in the form of:

$$HFP = \text{Antilog} \frac{EO_2 - EFt_2}{K_2} \quad 1)$$

$$HNOO = \text{Antilog} \frac{EHt_2 + 3.3 - EO_1}{K_1} \quad 2)$$

$$FAK = 4.339 - (1.769\ HNOO) = (0.5645\ HNOO^2) \quad 3)$$
$$- (0.1002\ HNOO^3) + (0.008698\ HNOO^4)$$
$$- (0.0002926\ HNOO^5)$$

$$HX = \frac{-9.976 + \sqrt{99.53\,[-] \pm (19.95\ HNOO)}}{.9547\ HNOO} \quad 4)$$

$$HNO_3 = \text{Antilog}\left[\left(\frac{EHt_2 + 3.3 - EO_1}{K_1}\right) - \right. \quad 5)$$
$$\left. - \left(\frac{HX \cdot FAK \cdot HNOO \cdot HFP}{K_1}\right)\right]$$

Substitute $HNO_3$ for $HNOO$ and solve equation 4) above for $HX^1$ \quad 6)

$$HF = HX^1 \cdot HNO_3 \cdot HFP \quad 7)$$

wherein:
   $EO_2$ and $EO_1$ are signals derived from the electrode voltages when in the calibration solution;
   $K_2$ and $K_1$ are signals derived from the electrode voltages when in the standardize solution; and
   $EFt_2$ and $EHt_2$ are signals derived from the electrode voltages when in the specimen solution and where HFP, HNOO, FAK, HX, $HX^1$ are operators in the form of electrical signals derived from said computation circuit means solving the relationships of formulas 1-7, and wherein $HNO_3$ is an electrical signal representing the concentration of a first acid in the specimen solution and HF is an electrical signal representing the concentration of a second acid in the specimen solution.

18. The instrument as defined in claim 17 wherein the weight of a known volume of a pickling bath specimen solution including HF and $HNO_3$ acids and metal ions is stored by said measurement control means and wherein said computation circuit means further generates electrical signals in the form of:

$$\%\ \text{Metal} = \frac{\left(\begin{array}{c}\text{gram weight of}\\ \text{100 cc of specimen}\end{array}\right) - \left[\begin{array}{c}ADK_1 \times HNO_3\ \text{Molar}\\ + ADK_2\ HF\ \text{Molar}\end{array}\right]}{\text{gram weight of 100 cc of specimen}}$$

where $ADK_1 = 3.33$ for $HNO_3$ and $ADK_2 = 0.57$ for HF and said percent metal by weight is displayed by said display means.

19. The instrument as defined in claim 18 wherein said operator programmable means comprises digital switch means coupled to said digital processing circuit.

20. In an acid testing instrument for determining the constituent acid concentration in a bath including a solution of more than one acid, means for determining, in addition, the metal content by weight of said bath comprising:

- means for storing the weight of a known volume of bath employed as the specimen by said instrument;
- circuit means including sensing means immersed in said bath for providing signals representative of the concentration of acids in said specimen;
- correlating means coupled to said circuit means for correlating signals representative of the weight of the known specimen volume with said signals representative of acid concentrations provided by said circuit means to provide difference output signals representative of the weight of the metal content of said bath; and
- display means coupled to said correlating means for displaying the metal content.

21. The instrument as defined in claim 22 wherein said correlating means generates electrical signals in the form of:

$$\% \text{ Metal} = \frac{\left(\begin{array}{c}\text{gram weight of}\\ \text{100 cc of specimen}\end{array}\right) - \left[\begin{array}{c}3.33 \times HNO_3 \text{ Molar}\\ + .57 \, HF \text{ Molar}\end{array}\right]}{\text{gram weight of 100 cc of specimen}}$$

for providing said output signals.

* * * * *

UNITED STATES PATENT AND TRADEMARK OFFICE
CERTIFICATE OF CORRECTION

Page 1 of 2

PATENT NO. : 4,060,717
DATED : November 29, 1977
INVENTOR(S) : George J. Sitek

It is certified that error appears in the above-identified patent and that said Letters Patent are hereby corrected as shown below:

Column 10; line 51:

"$HX = \dfrac{\div 9.976 + \sqrt{99.53 - (19.95\ HNOO)}}{.9547\ HNOO}$" should be --$HX = \dfrac{-9.976 + \sqrt{99.53 + (19.95\ HNOO)}}{.9547\ HNOO}$--

Column 16; line 3:
"alarm output means" should be --alarm means--

Column 16; line 4:
"alarm signal" should be --alarm output signal--

Column 16; equation 5:

"$HNO_3 = \text{Antilog}\left[\left(\dfrac{EHt_2 + 3.3 - EO_1}{K_1}\right) - \left(\dfrac{HX \cdot FAK \cdot HNOO \cdot HFP}{K_1}\right)\right]$" should be --$HNO_3 = \text{Antilog}\left[\left(\dfrac{EHt_2 + 3.3 - EO_1}{K_1}\right) - \left(\dfrac{HX \cdot FAK \cdot HNOO \cdot HFP}{K_1}\right)\right]$--

UNITED STATES PATENT AND TRADEMARK OFFICE
CERTIFICATE OF CORRECTION

PATENT NO. : 4,060,717
DATED : November 29, 1977
INVENTOR(S) : George J. Sitek

It is certified that error appears in the above-identified patent and that said Letters Patent are hereby corrected as shown below:

Column 18; line 6:
    "22" should be --20--

Signed and Sealed this

Fourth Day of July 1978

[SEAL]

Attest:

RUTH C. MASON
*Attesting Officer*

DONALD W. BANNER
*Commissioner of Patents and Trademarks*